United States Patent
Zeng et al.

(10) Patent No.: US 12,303,222 B2
(45) Date of Patent: May 20, 2025

(54) SURGICAL ROBOTIC ARM CONTROL SYSTEM AND CONTROL METHOD THEREOF

(71) Applicant: Metal Industries Research & Development Centre, Kaohsiung (TW)

(72) Inventors: Jian Jia Zeng, Kaohsiung (TW); Bo-Wei Pan, Kaohsiung (TW); Sheng-Hung Yang, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 263 days.

(21) Appl. No.: 17/992,864

(22) Filed: Nov. 22, 2022

(65) Prior Publication Data
US 2024/0164857 A1 May 23, 2024

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/10* (2016.02); *A61B 34/20* (2016.02); *A61B 34/70* (2016.02);
(Continued)

(58) Field of Classification Search
CPC ......... A61B 34/32; A61B 34/10; A61B 34/20; A61B 34/70; A61B 90/37;
(Continued)

(56) References Cited

U.S. PATENT DOCUMENTS

| | | |
|---|---|---|
| 2014/0276943 A1 | 9/2014 | Bowling et al. |
| 2015/0032164 A1 | 1/2015 | Crawford et al. |

(Continued)

FOREIGN PATENT DOCUMENTS

| | | | |
|---|---|---|---|
| CN | 115089302 | * | 9/2022 |
| TW | 201403277 | | 1/2014 |

OTHER PUBLICATIONS

"Office Action of Taiwan Counterpart Application", issued on Dec. 12, 2023, p. 1-p. 14.
(Continued)

*Primary Examiner* — Hien N Nguyen
(74) *Attorney, Agent, or Firm* — JCIPRNET

(57) ABSTRACT

A surgical robotic arm control system and a control method thereof are provided. The surgical robotic arm control system includes a surgical robotic arm, an image capture unit, and a processor. The image capture unit obtains a first image. The processor obtains a plurality of identification object coordinates of a plurality of identification object images according to the first image, and executes a virtual environment model to calculate a plurality of virtual spinal process coordinates of a virtual spine model. The processor generates surgical robotic arm operation information according to movement trajectory of a virtual surgical robotic arm moving toward a plurality of virtual identification objects located at the plurality of virtual spinal process coordinates in the virtual environment model, and controls the surgical robotic arm according to the surgical robotic arm operation information and the plurality of identification object coordinates.

18 Claims, 4 Drawing Sheets

(51) Int. Cl.
*A61B 34/10* (2016.01)
*A61B 34/20* (2016.01)
*A61B 90/00* (2016.01)
*G06V 10/82* (2022.01)

(52) U.S. Cl.
CPC .............. *A61B 90/37* (2016.02); *G06V 10/82* (2022.01); *A61B 2034/105* (2016.02); *A61B 2034/107* (2016.02); *A61B 2034/2057* (2016.02); *A61B 2034/2065* (2016.02); *A61B 2090/3762* (2016.02)

(58) Field of Classification Search
CPC ........ A61B 2034/105; A61B 2034/107; A61B 2034/2057; A61B 2034/2065; A61B 2090/3762; A61B 34/30; A61B 90/361; G06V 10/82; G06V 2201/03
See application file for complete search history.

(56) References Cited

U.S. PATENT DOCUMENTS

| | | | |
|---|---|---|---|
| 2017/0084027 A1* | 3/2017 | Mintz | A61B 1/2676 |
| 2019/0327394 A1* | 10/2019 | Ramirez Luna | H04N 23/51 |
| 2020/0023521 A1* | 1/2020 | Dan | B25J 9/1692 |
| 2020/0082522 A1* | 3/2020 | Bonneau | G06V 10/764 |
| 2020/0094405 A1 | 3/2020 | Davidson et al. | |
| 2022/0047335 A1 | 2/2022 | Morgan et al. | |
| 2022/0287676 A1 | 9/2022 | Steines et al. | |

OTHER PUBLICATIONS

"Office Action of Taiwan Counterpart Application", issued on Aug. 9, 2023, p. 1-p. 13.

* cited by examiner

SURGICAL ROBOTIC ARM CONTROL SYSTEM AND CONTROL METHOD THEREOF

BACKGROUND OF THE INVENTION

Field of the Invention

The invention relates to a control system, and in particular, to a surgical robotic arm control system and a control method thereof.

Description of Related Art

Surgical robotic arms have been widely used in various medical operations, and may be used to assist medical personnel in related surgical operations. Accordingly, the surgical robotic arm may be used, for example, to avoid unnecessary wounds of a surgical target caused by the tremor of the hands of the medical personnel during the surgical operation, in order to help effectively reduce blood loss, reduce wounds, reduce pain, shorten hospital days, reduce the risk of postoperative infection, and speed up the recovery of the surgical target after surgery, etc. However, in existing surgical robotic arm control applications, the operation of the surgical robotic arm usually still needs to be moved and controlled as a whole by medical personnel, which is prone to operation errors and low operation efficiency.

SUMMARY OF THE INVENTION

The invention provides a surgical robotic arm control system and a control method thereof that may effectively control a surgical robotic arm, so as to effectively assist an operator to perform related surgical tasks during surgery.

A surgical robotic arm control system of the invention includes a surgical robotic arm, an image capture unit, and a processor. The image capture unit is configured to obtain a first image. The first image includes a plurality of identification object images of a plurality of identification objects. The processor is coupled to the surgical robotic arm and the image capture unit. The processor obtains a plurality of identification object coordinates of the plurality of identification object images according to the first image. The processor executes a virtual environment model to calculate a plurality of virtual spinal process coordinates of the virtual spine model. The processor generates surgical robotic arm operation information according to movement trajectory of a virtual surgical robotic arm moving toward a plurality of virtual identification objects located at the plurality of virtual spinal process coordinates in the virtual environment model. The processor controls the surgical robotic arm according to the surgical robotic arm operation information and the plurality of identification object coordinates.

A surgical robotic arm control method of the invention includes the following steps: obtaining a first image via an image capture unit, wherein the first image includes a plurality of identification object images of a plurality of identification objects; obtaining a plurality of identification object coordinates of the plurality of identification object images according to the first image; executing a virtual environment model to calculate a plurality of virtual spinal process coordinates of the virtual spine model; generating surgical robotic arm operation information according to movement trajectory of a virtual surgical robotic arm moving toward a plurality of virtual identification objects located at the plurality of virtual spinal process coordinates in the virtual environment model; and controlling a surgical robotic arm according to the surgical robotic arm operation information and the plurality of identification object coordinates.

Based on the above, the surgical robotic arm control system and the control method thereof of the invention may automatically control the surgical robotic arm to move to a nearby position adjacent to the surgical target and automatically adjust the posture of the surgical robotic arm, in order to effectively assist the operator to perform related surgical tasks during surgery.

In order to make the aforementioned features and advantages of the disclosure more comprehensible, embodiments accompanied with figures are described in detail below.

DESCRIPTION OF THE EMBODIMENTS

Figure 1:
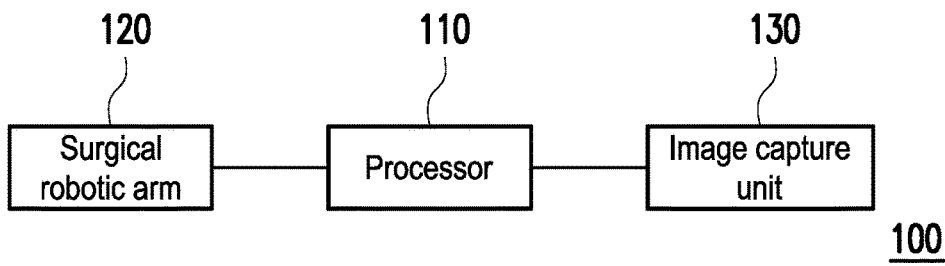
FIG. 1 is a schematic diagram of a surgical robotic arm control system according to an embodiment of the invention.

To make the contents of the invention more easily understood, embodiments are provided below as examples of the plausibility of implementation of the disclosure. Moreover, when applicable, elements/components/steps having the same reference numerals in figures and embodiments represent the same or similar parts.

FIG. 1 is a schematic diagram of a surgical robotic arm control system according to an embodiment of the invention. Referring to FIG. 1, a surgical robotic arm control system 100 includes a processor 110, a surgical robotic arm 120, and an image capture unit 130. The processor 110 is coupled to the surgical robotic arm 120 and the image capture unit 130. In the present embodiment, the surgical robotic arm control system 100 may be disposed, for example, in an operating room or other surgical environments, and may provide auxiliary functions during surgery performed by medical staff.

In the present embodiment, the processor 110 may, for example, be disposed in an electronic equipment having computing function such as a personal computer (PC), a notebook computer, a tablet computer, an industrial computer, an embedded computer, or a cloud server, but the invention is not limited thereto.

In the present embodiment, the surgical robotic arm 120 may include at least three joint axes, for example, to achieve a robotic arm having six degrees of freedom in space. In the present embodiment, the processor 110 may control the surgical robotic arm 120, and achieve forward kinematics and inverse kinematics of the robotic arm. In the present embodiment, the image capture unit 130 may be a depth camera, and generates RGB digital image information and depth image information.

In the present embodiment, the surgical robotic arm control system 100 may further include a display (not shown). The processor 110 is coupled to the display. In the present embodiment, the surgical robotic arm control system 100 may further include a storage device (not shown). The processor 110 is coupled to the storage device. The storage device may include a memory, wherein the memory may be, for example, non-volatile memory such as read-only memory (ROM) or erasable programmable read-only memory (EPROM), volatile memory such as random-access memory (RAM), or memory such as hard disc drive or semiconductor memory, and configured to store various modules, images, information, parameters, and data mentioned in the invention. In the present embodiment, the storage device may, for example, store a panoramic environment field positioning module, an object image detection model, a virtual environment model, a robotic arm motion database, and a robotic arm automatic control module, etc., which may be read and executed by the processor 110, so as to achieve the surgical robotic arm control function described in each embodiment of the invention.

In the present embodiment, the processor 110 may be connected to the surgical robotic arm 120 via a connection method such as Internet Protocol, Universal Serial Bus (USB), and Type-C USB, and execute the robotic arm automatic control module to control the surgical robotic arm 120. In the present embodiment, the virtual environment model may be, for example, software such as V-Rep or MuJoCo, and a virtual surgical robotic arm, a virtual spine model, and a virtual identification object and the like may be placed in the virtual environment.

Figure 2:
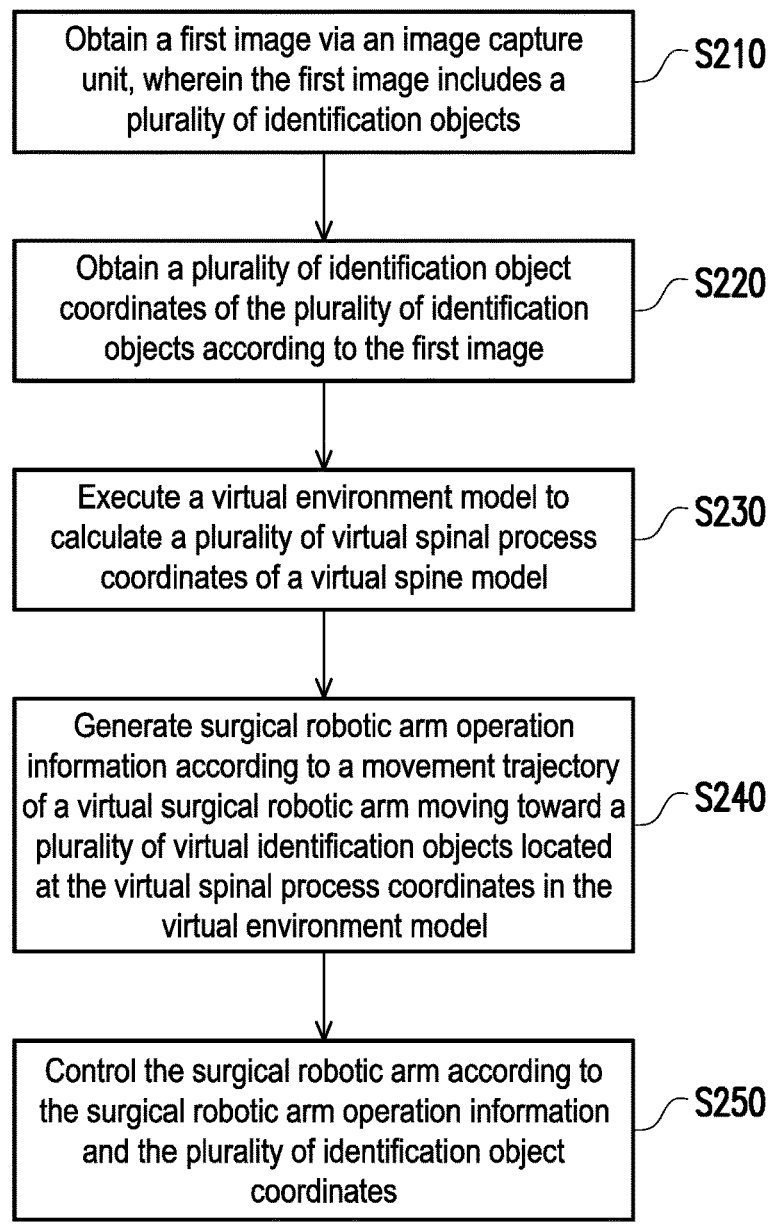
FIG. 2 is a flowchart of a surgical robotic arm control method according to an embodiment of the invention.
Figure 3:
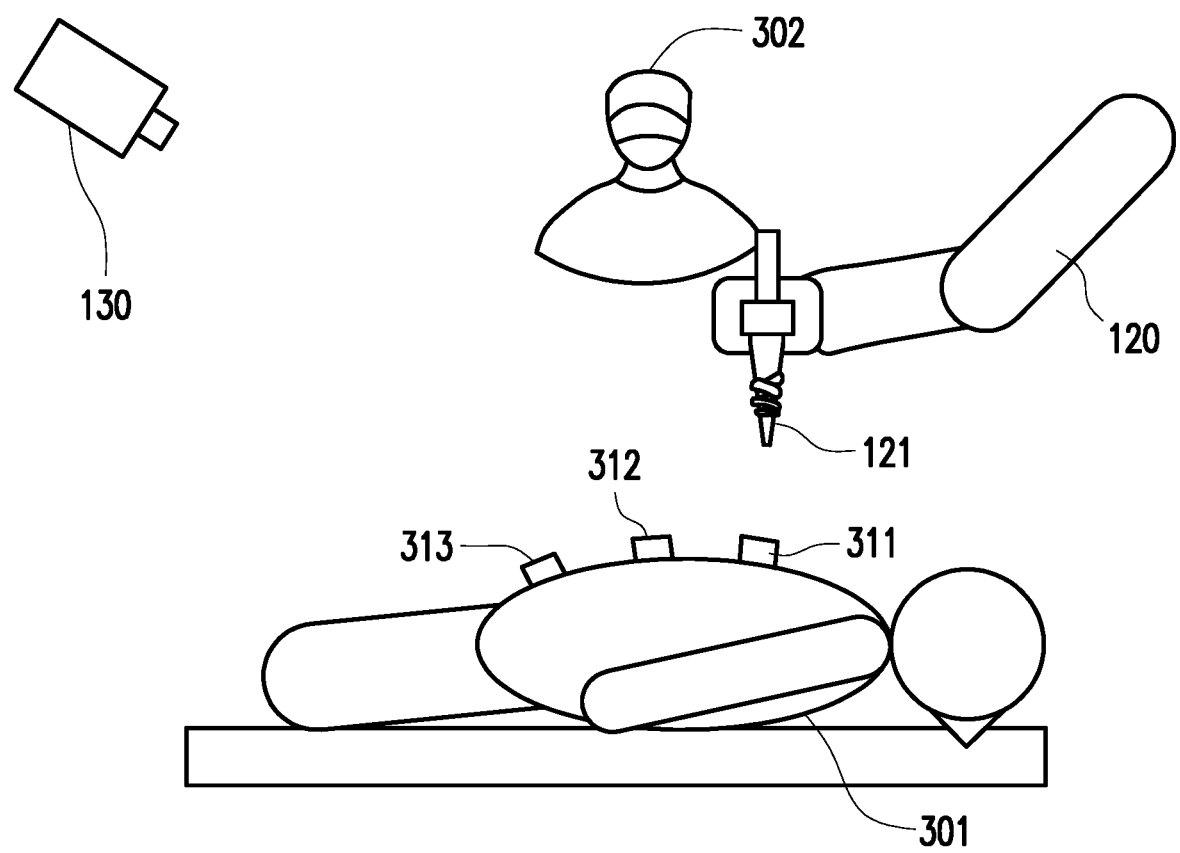
FIG. 3 is a schematic diagram of an operation scene of a surgical robotic arm according to an embodiment of the invention.

FIG. 2 is a flowchart of a surgical robotic arm control method according to an embodiment of the invention. FIG. 3 is a schematic diagram of an operation scene of a surgical robotic arm according to an embodiment of the invention. Referring to FIG. 1 to FIG. 3, the surgical robotic arm control system 100 may perform the following steps S210 to S250 to control the surgical robotic arm 120 and assist a medical personnel 302 to perform a preoperative spinal process drilling operation in orthopedic medicine. First, as shown in FIG. 3, a surgical target 301 may face down and lie flat on an operating platform (fixed work platform), and the surgical robotic arm 120 and the image capture unit 130 may be disposed around the operating platform. A plurality of identification objects 311 to 313 may be placed on a plurality of spinal process positions of the spine of the operation target 301. In an embodiment, the number of identification objects may be one. In other embodiments, the number of identification objects may also be two or more.

In step S210, the processor 110 may operate the image capture unit 130 to obtain a first image via the image capture unit 130, wherein the first image includes a plurality of identification object images of the identification objects 311 to 313. In step S220, the processor 110 may obtain a plurality of identification object coordinates of the plurality of identification object images according to the first image. In the present embodiment, the first image may include RGB digital image data and depth image data. The processor 110 may execute the object image detection model to identify the identification object images and the positions thereof in the RGB digital image data. In the present embodiment, the processor 110 may analyze the first image to identify a plurality of identification object images in the first image according to a feature identification parameter such as identification object thickness, identification object size, and image capture azimuth angle, etc., and obtain a plurality of corresponding identification object coordinates of the identification objects 311 to 313 in the robotic arm world coordinate system.

In an embodiment, the processor 110 may calculate the distance between any two identification objects, and/or the distance between the surgical robotic arm 120 and any two identification objects, respectively, as a distance verification of the virtual identification objects in the subsequent virtual environment. For example, as shown in FIG. 3, the processor 110 may calculate a first distance between the identification object 311 and the identification object 312, a second distance between the identification object 311 and the identification object 313, and a third distance between the identification object 312 and the identification object 313. In addition, the processor 110 may also calculate a fourth distance between any identification object and the surgical robotic arm. Next, the processor 110 may perform various corresponding relative distance calculations and/or parameter conversions according to the first distance, the second distance, the third distance, and the fourth distance, in order to correct the plurality of identification object coordinates of the identification objects 311 to 313 in the robotic arm world coordinate system.

In the present embodiment, the object image detection model may include a trained convolutional neural network model. The convolutional neural network model may, for example, include a fully convolutional neural network (FCN) model, and may be trained by a deep learning algorithm in advance. In an embodiment, the object image detection model may also be implemented by a model such as VCG-16, Inception Net, ResNet, and Densenet. The processor 110 may execute a convolutional neural network model to identity a plurality of identification object images in the first image. The processor 110 may input the first image to the convolutional neural network model, so that the convolutional neural network model may output a plurality of identification object images of the identification objects 311 to 313. Next, the processor 110 may superimpose the plurality of identification object images on the robotic arm world coordinate system to obtain the plurality of corresponding identification object coordinates of the identification objects 311 to 313 in the robotic arm world coordinate system.

Figure 4:
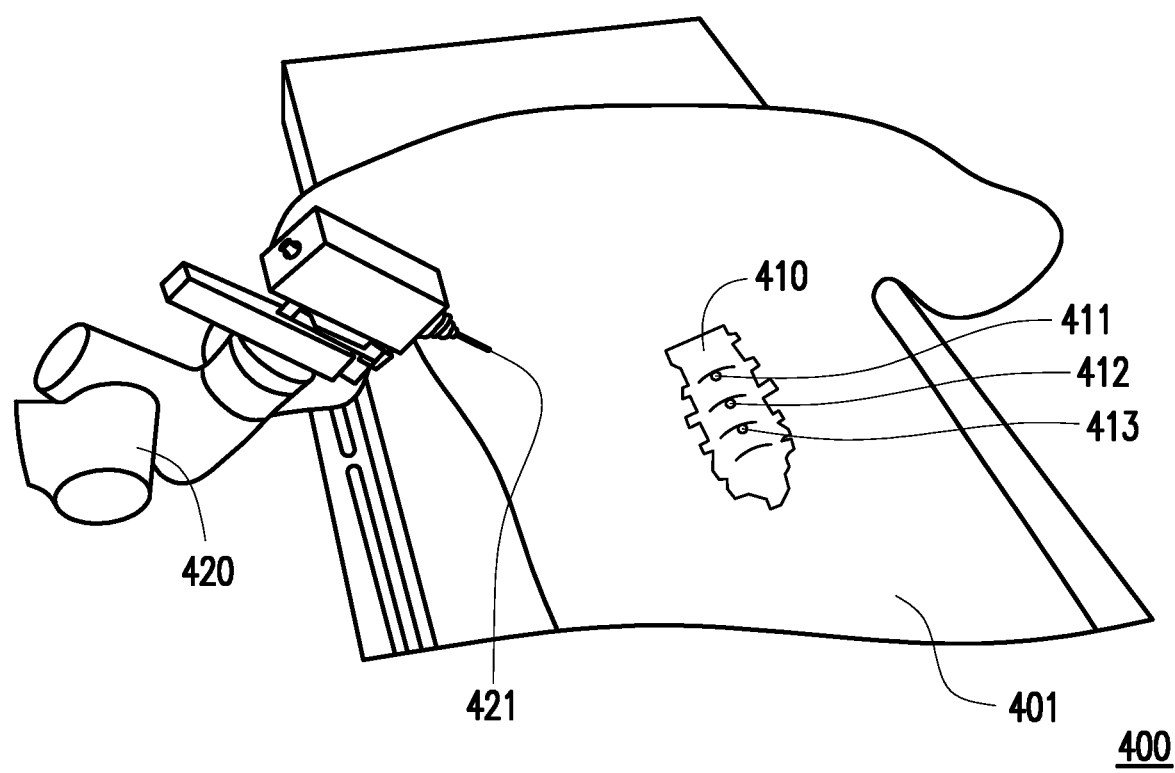
FIG. 4 is a schematic diagram of a virtual environment according to an embodiment of the invention.

In step S230, the processor 110 may execute a virtual environment model to calculate a plurality of virtual spinal process coordinates of the virtual spine model. Accordingly, also referring to FIG. 4, FIG. 4 is a schematic diagram of a virtual environment according to an embodiment of the invention. In the present embodiment, the processor 110 may execute a spinal medical image processing module to convert the spinal medical image of the surgical target 301 into a virtual spine model 410 in advance, and calibrate a converted coordinate value to calculate a plurality of operating parameters according to the converted coordinate value and the virtual spine model 410. A virtual environment 400 (virtual three-dimensional world) includes a virtual surgical target 401, the virtual spine model 410, and a virtual surgical robotic arm 420. The virtual spine model 410 is placed at a preset position in the virtual surgical target 401. In the present embodiment, the spinal medical image may be, for example, a computed tomography scan (CT scan) image or other medical images conforming to the Digital Imaging and Communications in Medicine (DICOM) protocol.

In the present embodiment, the processor 110 may calculate a plurality of operating parameters according to the converted coordinate value and the virtual spine model 410. The processor 110 may calculate a mapping function of a virtual spine model coordinate system and a virtual environment coordinate system according to the converted coordinate value on the virtual spine model 410, so that the coordinate values of a plurality of virtual identification objects 411 to 413 located on the plurality of dorsal spinal process identification points in the virtual environment 400 may be mapped back to the virtual spine model coordinate system and the spinal medical image of the surgical target 301 according to the mapping function. The processor 110 may obtain the spinal process coordinate value thereof in the virtual robotic arm world coordinate system, and return the spinal process coordinate value to the spinal medical image via the converted coordinate value, and frame the spatial range of the spinal process of the virtual spine model 410 according to the preset fixed distance to calculate a plurality of operating parameters, wherein the plurality of operating parameters may include, for example, drilling entry angle and drilling spinal process Z-axis height. Moreover, the processor 110 may match the plurality of identification object coordinates of the identification object images to the plurality of virtual spinal process coordinates in the virtual environment 400 to obtain a coordinate conversion parameter.

Figure 5:
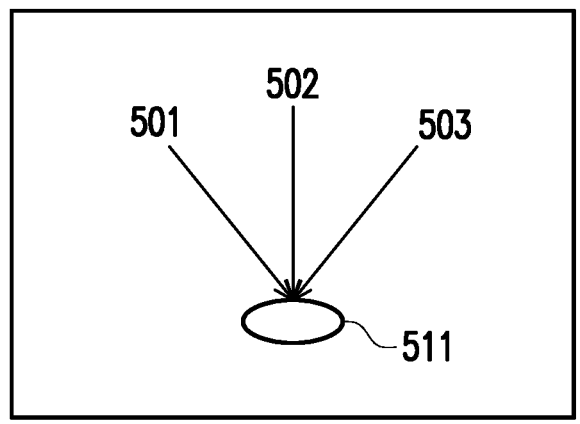
FIG. 5 is a schematic diagram of indicator icons according to an embodiment of the invention.

In step S240, the processor 110 may generate surgical robotic arm operation information according to the movement trajectory of the virtual surgical robotic arm 420 moving toward the plurality of virtual identification objects 411 to 413 located at the plurality of virtual spinal process coordinates in the virtual environment model. Referring to FIG. 5, FIG. 5 is a schematic diagram of indicator icons according to an embodiment of the invention. In the present embodiment, the surgical robotic arm control system 100 may further include a display. The processor 110 may be coupled to the display and drive the display to display the virtual environment image of the virtual environment 400. The processor 110 may display a plurality of corresponding indicator icons 501 to 503 corresponding to a dorsal spinal process identification point 511 of the virtual identification object 411 in the virtual environment 400 as shown in FIG. 5 in the virtual environment image according to the plurality of operating parameters. The medical personnel 302 may view the virtual environment image in the operation interface displayed on the display and refer to the indicator icons 501 to 503 to control the virtual surgical robotic arm 420 of the virtual environment 400 to move, for example, via an input device (such as a mouse and a keyboard). The processor 110 may record the surgical robotic arm operation information of the movement result of the virtual surgical robotic arm 420 in the virtual environment 400. The surgical robotic arm operation information may include the movement position and the joint axis angle of the surgical robotic arm.

In step S250, the processor 110 may control the surgical robotic arm according to the surgical robotic arm operation information and the plurality of identification object coordinates. In the present embodiment, the processor 110 may read the robotic arm motion database according to the plurality of operating parameters and the surgical robotic arm operation information to obtain control information configured to control the surgical robotic arm 120. The robotic arm motion database may be mechanically pre-established and stored in the storage device of the surgical robotic arm control system 100. The robotic arm motion database may record the movement trajectory of the virtual surgical robotic arm 420 in the virtual environment simulating the real environment, wherein the movement trajectory is the control information of a virtual drilling equipment 421 (i.e., the end original position) of the robotic arm end of the virtual surgical robotic arm 420 respectively moving above the virtual identification objects 411 to 413. In this regard, the control information may be the movement trajectory information and the end posture information of the virtual surgical robotic arm 420.

In other words, the surgical robotic arm control system 100 may simulate a real surgical environment to simulate a drilling operation, and may control the surgical robotic arm according to the coordinate conversion parameter and the control information. In the present embodiment, the processor 110 may execute the robotic arm automatic control module to read the control information from the robotic arm motion database to the robotic arm in the real environment according to the confirmed robotic arm end movement position and the wrist joint axis angle, and operate the surgical robotic arm 120. The processor 110 may import the previously stored movement coordinate value control information of the robotic arm end of the surgical robotic arm 120 into the surgical robotic arm 120, so as to run forward and reverse kinematics of the robotic arm. In this way, the surgical robotic arm 120 may be automatically restored to perform related robotic arm operations such as movement trajectory, movement position, and wrist axis angle of the virtual drilling equipment 421 of the robotic arm end of the virtual robotic arm 420 in the virtual environment 400. Therefore, the surgical robotic arm 120 may be correspondingly automatically moved to, for example, a position adjacent to the spinal process corresponding to the identification object 311 according to the operation of the virtual surgical robotic arm 420 in the virtual environment 400, and change the posture in advance so that the drilling equipment of the robotic arm end may present an appropriate drilling angle. Accordingly, the medical personnel 302 may continue to operate the surgical robotic arm 120 in the real world, so as to accurately and quickly perform a preoperative spinal process drilling operation.

In addition, in the present embodiment, the surgical robotic arm control system 100 may pre-establish a robotic arm world coordinate system of the surgical robotic arm 120. The processor 110 may photograph the surgical robotic arm 120 and a positioning object via the image capture unit 130 to obtain a reference image. The processor 110 may execute a panoramic environment field positioning module to perform image analysis on the reference image according to a focal length parameter and a coordinate rotation matrix provided by the image capture unit 130, to determine the relative position of the image capture unit 130 located in the robotic arm world coordinate system. The positioning object may be preset at the position of the drilling equipment 121 at the robotic arm end of the surgical robotic arm 120, for example, and may be, for example, a positioning plate having a checkerboard pattern. In this way, the processor 110 may project the robotic arm world coordinate system to the subsequently obtained first image according to the focal length parameter, so as to accurately superimpose the first image into the robotic arm world coordinate system. The processor 110 may correspondingly obtain the identification object coordinates of the identification objects 311 to 313 in the robotic arm world coordinate system according to the positions of the identification object images in the first image.

Based on the above, the surgical robotic arm control system and the control method thereof of the invention may allow medical personnel to operate the virtual surgical robotic arm of the virtual environment to move to the adjacent position of the virtual identification object in advance, and the virtual drilling equipment of the robotic arm end may present a specific appropriate drilling angle.

Next, the surgical robotic arm control system may automatically control the surgical robotic arm to move to a nearby position adjacent to the surgical target, and automatically adjust the posture of the drilling equipment of the robotic arm end of the surgical robotic arm. In this way, medical personnel may quickly and accurately manually control the drilling equipment of the robotic arm end the surgical robotic arm to perform corresponding surgical operations. Therefore, the surgical robotic arm control system and the control method thereof of the invention may effectively assist the operator to perform related surgical tasks. The surgical robotic arm control system and the control method thereof of the invention may effectively reduce the probability of operating errors of the surgical robotic arm, and may improve the operation efficiency of the surgical robotic arm.

Although the invention has been described with reference to the above embodiments, it will be apparent to one of ordinary skill in the art that modifications to the described embodiments may be made without departing from the spirit of the disclosure. Accordingly, the scope of the disclosure is defined by the attached claims not by the above detailed descriptions.

What is claimed is:

1. A surgical robotic arm control system, comprising:
   a surgical robotic arm;
   a camera configured to obtain a first image, wherein the first image comprises a plurality of identification object images of a plurality of identification objects; and
   a processor coupled to the surgical robotic arm and the camera,
   wherein the processor obtains a plurality of identification object coordinates of the plurality of identification object images according to the first image, and the processor executes a virtual environment model to calculate a plurality of virtual spinal process coordinates of a virtual spine model,
   wherein the processor generates surgical robotic arm operation information according to movement trajectory of a virtual surgical robotic arm moving toward a plurality of virtual identification objects located at the plurality of virtual spinal process coordinates in the virtual environment model, and the processor controls the surgical robotic arm according to the surgical robotic arm operation information and the plurality of identification object coordinates,
   wherein a number of the plurality of identification object coordinates is greater than or equals to three, and wherein the processor calculates first distance based on first identification object coordinate and second identification object coordinate, calculates second distance based on the first identification object coordinate and third identification object coordinate, calculates third distance based on the second identification object coordinate and the third identification object coordinate, calculates fourth distance based on the first identification object coordinate and a surgical robotic arm coordinate, and corrects the plurality of identification object coordinates based on the first distance, the second distance, the third distance and the fourth distance,
   wherein the processor obtains the plurality of identification object coordinates based on identification of feature identification parameters of the plurality of identification object images in the first image.

2. The surgical robotic arm control system of claim 1, wherein the processor photographs the surgical robotic arm and a positioning object via the camera to obtain a reference image, and the processor performs an image analysis on the reference image according to a focal length parameter and a coordinate rotation matrix, so as to determine a relative position of the camera located in a robotic arm world coordinate system.

3. The surgical robotic arm control system of claim 1, wherein the processor executes a convolutional neural network model to identify the plurality of identification object images in the first image, and superimposes the plurality of identification object images to a robotic arm world coordinate system to obtain the plurality of identification object coordinates.

4. The surgical robotic arm control system of claim 1, wherein the processor converts a spinal medical image into the virtual spine model, and calibrates a converted coordinate value to calculate a plurality of operating parameters according to the converted coordinate value and the virtual spine model,
   wherein the processor reads a robotic arm motion database according to the plurality of operating parameters and the surgical robotic arm operation information, so as to obtain control information configured to control the surgical robotic arm.

5. The surgical robotic arm control system of claim 4, wherein the processor matches the plurality of identification object coordinates of the plurality of identification object images to the plurality of virtual spinal process coordinates in the virtual environment model to obtain a coordinate conversion parameter, and the processor controls the surgical robotic arm according to the coordinate conversion parameter and the control information.

6. The surgical robotic arm control system of claim 4, wherein the processor controls the surgical robotic arm to move adjacent to one of the plurality of identification objects, and controls an end posture of the surgical robotic arm to correspond to the plurality of operating parameters.

7. The surgical robotic arm control system of claim 4, wherein the processor drives a display to display a virtual environment image of the virtual environment model, and the processor displays a plurality of corresponding indicator icons on the virtual environment image according to the plurality of operating parameters.

8. The surgical robotic arm control system of claim 4, wherein the plurality of operating parameters comprise a drilling entry angle and a drilling spinal process height.

9. The surgical robotic arm control system of claim 4, wherein the spinal medical image is a computed tomography scan image.

10. A surgical robotic arm control method, comprising:
    obtaining a first image via a camera, wherein the first image comprises a plurality of identification object images of a plurality of identification objects;
    obtaining a plurality of identification object coordinates of the plurality of identification object images according to the first image;
    executing a virtual environment model to calculate a plurality of virtual spinal process coordinates of a virtual spine model;
    generating surgical robotic arm operation information according to movement trajectory of a virtual surgical robotic arm moving toward a plurality of virtual identification objects located at the plurality of virtual spinal process coordinates in the virtual environment model; and
    controlling a surgical robotic arm according to the surgical robotic arm operation information and the plurality of identification object coordinates, wherein a number of the plurality of identification object coordinates is greater than or equals to three, and wherein a processor calculates first distance based on first identification object coordinate and second identification object coordinate, calculates second distance based on the first identification object coordinate and third identification object coordinate, calculates third distance based on the second identification object coordinate and the third identification object coordinate, calculates fourth distance based on the first identification object coordinate and a surgical robotic arm coordinate, and corrects the plurality of identification object coordinates based on the first distance, the second distance, the third distance and the fourth distance, wherein the plurality of identification object coordinates are obtained based on identification of feature identification parameters of the plurality of identification object images in the first image.

11. The surgical robotic arm control method of claim 10, further comprising:
  photographing the surgical robotic arm and a positioning object via the camera to obtain a reference image; and
  performing an image analysis on the reference image according to a focal length parameter and a coordinate rotation matrix to determine a relative position of the camera located in a robotic arm world coordinate system.

12. The surgical robotic arm control method of claim 10, wherein the step of obtaining the plurality of identification object coordinates of the plurality of identification object images according to the first image comprises:
  executing a convolutional neural network model to identify the plurality of identification object images in the first image; and
  superimposing the plurality of identification object images on a robotic arm world coordinate system to obtain the plurality of identification object coordinates.

13. The surgical robotic arm control method of claim 10, wherein the step of controlling the surgical robotic arm according to the surgical robotic arm operation information and the plurality of identification object coordinates comprises:
  converting a spinal medical image into the virtual spine model, and calibrating a converted coordinate value to calculate a plurality of operating parameters according to the converted coordinate value and the virtual spine model; and
  reading a robotic arm motion database according to the plurality of operating parameters and the surgical robotic arm operation information, so as to obtain control information configured to control the surgical robotic arm.

14. The surgical robotic arm control method of claim 13, wherein the step of controlling the surgical robotic arm according to the surgical robotic arm operation information and the plurality of identification object coordinates further comprises:
  matching the plurality of identification object coordinates of the plurality of identification object images to the plurality of virtual spinal process coordinates in the virtual environment model to obtain a coordinate conversion parameter; and
  controlling the surgical robotic arm according to the coordinate conversion parameter and the control information.

15. The surgical robotic arm control method of claim 13, wherein the step of controlling the surgical robotic arm according to the surgical robotic arm operation information and the plurality of identification object coordinates further comprises:
  controlling the surgical robotic arm to move adjacent to one of the plurality of identification objects; and
  controlling an end posture of the surgical robotic arm to correspond to the plurality of operating parameters.

16. The surgical robotic arm control method of claim 13, further comprising:
  displaying a virtual environment image of the virtual environment model via a display; and
  displaying a plurality of corresponding indicator icons in the virtual environment image according to the plurality of operating parameters.

17. The surgical robotic arm control method of claim 13, wherein the plurality of operating parameters comprise a drilling entry angle and a drilling spinal process height.

18. The surgical robotic arm control method of claim 13, wherein the spinal medical image is a computed tomography scan image.

* * * * *